United States Patent [19]
Ogle

[11] Patent Number: 6,113,636
[45] Date of Patent: *Sep. 5, 2000

[54] MEDICAL ARTICLE WITH ADHERED ANTIMICROBIAL METAL

[75] Inventor: Matthew F. Ogle, St. Paul, Minn.

[73] Assignee: St. Jude Medical, Inc., St. Paul, Minn.

[*] Notice: This patent issued on a continued prosecution application filed under 37 CFR 1.53(d), and is subject to the twenty year patent term provisions of 35 U.S.C. 154(a)(2).

[21] Appl. No.: 08/974,992

[22] Filed: Nov. 20, 1997

[51] Int. Cl.[7] .................. A61F 2/02; A61F 2/24; A61F 27/00; A61F 27/04
[52] U.S. Cl. .................. 623/11.11; 623/2.13; 623/23.72; 427/2.24
[58] Field of Search .................. 623/1–3, 11, 12, 623/16; 427/2.24

[56] References Cited

U.S. PATENT DOCUMENTS

| | | |
|---|---|---|
| Re. 32,449 | 6/1987 | Claussen et al. . |
| 3,643,658 | 2/1972 | Steinemann . |
| 3,707,006 | 12/1972 | Bokros et al. . |
| 4,040,129 | 8/1977 | Steinemann et al. . |
| 4,054,139 | 10/1977 | Crossley . |
| 4,132,746 | 1/1979 | Urry et al. . |
| 4,145,764 | 3/1979 | Suzuki et al. . |
| 4,159,358 | 6/1979 | Hench et al. . |
| 4,187,852 | 2/1980 | Urry et al. . |
| 4,223,412 | 9/1980 | Aoyagi et al. . |
| 4,253,463 | 3/1981 | Kim . |
| 4,411,041 | 10/1983 | Braga . |
| 4,411,648 | 10/1983 | Davis et al. . |
| 4,418,686 | 12/1983 | Child . |
| 4,456,589 | 6/1984 | Holman et al. . |
| 4,476,590 | 10/1984 | Scales et al. . |
| 4,479,795 | 10/1984 | Mustacich et al. . |
| 4,483,678 | 11/1984 | Nishio et al. . |
| 4,483,688 | 11/1984 | Akiyama . |
| 4,495,664 | 1/1985 | Blanquaert . |
| 4,500,700 | 2/1985 | Urry . |
| 4,563,485 | 1/1986 | Fox, Jr. et al. . |
| 4,564,361 | 1/1986 | Akiyama . |
| 4,569,673 | 2/1986 | Tesi . |

(List continued on next page.)

FOREIGN PATENT DOCUMENTS

| | | |
|---|---|---|
| 0 206 024 | 6/1986 | European Pat. Off. . |
| 0 251 783 | 7/1987 | European Pat. Off. . |
| 2 575 387 | of 1985 | France . |
| 2 576 793 | of 1985 | France . |
| 37 22 410 | of 1988 | Germany . |
| WO/91/04073 | 4/1991 | WIPO . |
| WO 92/11043 | 7/1992 | WIPO . |
| WO 95/13704 | 5/1995 | WIPO . |
| WO 98/31404 | 7/1997 | WIPO . |
| WO 97/27886 | 8/1997 | WIPO . |

OTHER PUBLICATIONS

Butcher, Jr., et al., The Journal of Trauma, vol. 9, No. 5, pp. 359–376 (1969).

Chervu et al., Journal of Vascular Surgery, vol. 13, pp. 897–901 (1991).

(List continued on next page.)

*Primary Examiner*—Mickey Yu
*Assistant Examiner*—Choon P. Koh
*Attorney, Agent, or Firm*—Hallie A. Finucane; Peter S. Dardi; Westman, Champlin & Kelly, P.A.

[57] ABSTRACT

Approaches are described for depositing antimicrobial elemental metal and/or metal compounds within a medical article. The medical article generally includes biocompatible material that can contact bodily fluids. In particular, antimicrobial elemental metal can be deposited on and in a biocompatible material such as tissue. Chemical, photochemical and electrochemical processes for depositing elemental metal are described. In addition, an antimicrobial metal compound can be deposited by precipitation of the compound from a solution of metal cation. Antimicrobial metal deposits may reduce the incidence of infection associated with contacting a recipient medical patient with the biocompatible material.

20 Claims, 4 Drawing Sheets

U.S. PATENT DOCUMENTS

| | | |
|---|---|---|
| 4,581,028 | 4/1986 | Fox, Jr. et al. . |
| 4,589,882 | 5/1986 | Urry . |
| 4,592,920 | 6/1986 | Murtfeldt . |
| 4,603,152 | 7/1986 | Laurin et al. . |
| 4,612,337 | 9/1986 | Fox, Jr. et al. . |
| 4,615,705 | 10/1986 | Scales et al. . |
| 4,636,218 | 1/1987 | Fukuura et al. . |
| 4,687,487 | 8/1987 | Hintermann . |
| 4,693,718 | 9/1987 | Urry et al. . |
| 4,783,523 | 11/1988 | Urry et al. . |
| 4,801,299 | 1/1989 | Brendel et al. . |
| 4,846,844 | 7/1989 | DeLeon et al. . |
| 4,870,055 | 9/1989 | Urry et al. . |
| 4,886,505 | 12/1989 | Haynes et al. . |
| 4,902,503 | 2/1990 | Umemura et al. . |
| 4,923,450 | 5/1990 | Maeda et al. . |
| 4,933,178 | 6/1990 | Capelli . |
| 4,973,320 | 11/1990 | Brenner et al. . |
| 4,976,734 | 12/1990 | Urry et al. . |
| 5,019,096 | 5/1991 | Fox, Jr. et al. . |
| 5,037,438 | 8/1991 | Davidson . |
| 5,049,139 | 9/1991 | Gilchrist . |
| 5,049,140 | 9/1991 | Brenner et al. . |
| 5,059,186 | 10/1991 | Yamamoto et al. . |
| 5,064,430 | 11/1991 | Urry . |
| 5,123,924 | 6/1992 | Sioshansi et al. . |
| 5,156,613 | 10/1992 | Sawyer . |
| 5,207,706 | 5/1993 | Menaker . |
| 5,209,776 | 5/1993 | Bass et al. . |
| 5,223,420 | 6/1993 | Rabaud et al. . |
| 5,254,113 | 10/1993 | Wilke . |
| 5,292,362 | 3/1994 | Bass et al. . |
| 5,295,979 | 3/1994 | Delaurentis et al. . |
| 5,320,908 | 6/1994 | Sodervall et al. . |
| 5,324,275 | 6/1994 | Raad et al. . |
| 5,336,256 | 8/1994 | Urry . |
| 5,336,616 | 8/1994 | Livesey et al. . |
| 5,368,608 | 11/1994 | Levy et al. ................................. 623/2 |
| 5,409,467 | 4/1995 | Raad et al. . |
| 5,454,886 | 10/1995 | Burrell et al. ............................ 623/66 |
| 5,468,562 | 11/1995 | Farivar et al. . |
| 5,474,797 | 12/1995 | Sioshansi et al. . |
| 5,492,763 | 2/1996 | Barry et al. . |
| 5,498,248 | 3/1996 | Milder . |
| 5,516,480 | 5/1996 | Krall et al. . |
| 5,520,664 | 5/1996 | Bricault, Jr. et al. . |
| 5,630,804 | 5/1997 | Imada et al. . |
| 5,662,913 | 9/1997 | Capelli . |
| 6,013,106 | 1/2000 | Tweeden ................................. 623/66 |

OTHER PUBLICATIONS

Clark, et al., Arch. Surg., vol. 109, pp. 159–162 (Aug. 1974).

Babycos et al., Journal of Parenteral and Enteral Nutrition, vol. 17, No. 1, pp. 61–63 (1993).

Bambauer et al., ASAIO Journal, vol. 38, No. 2, pp. 96–101 (1992).

Bambauer et al., Dialysis & Transplantation, vol. 24, No. 5, pp. 228–237 (May 1995).

Deitch et al., The Journal of Trauma, vol. 29, No. 4, pp. 430–434 (Apr. 1989).

Dunkirk et al., Journal of Biomaterials Applications, vol. 6, pp. 131–156 (Oct. 1991).

French et al., The Journal of Thoracic and Cardiovascular Surgery, vol. 112, No. 2, pp. 248–252 (Aug. 1996).

Gravens et al., Surgery, vol. 73, No. 1, pp. 122–127 (Jan. 1973).

Grier, Nathaniel, in Disinfection, Sterilization, and Preservation, Chapter 20–Silver and Its Compounds, pp. 395–407.

Haynes, et al., Proceedings of the First International Conference on Gold and Silver in Medicine, Bethesda, Maryland, pp. 331 (Abstract), May 13–14, 1987.

Jansen et al., Journal of Biomaterials Applications, vol. 9, pp. 55–70 (Jul. 1994).

Kinney et al., Journal of Surgical Research, vol. 50, pp. 430–435 (1991).

Liedberg et al., Urol. Res., vol. 17, pp. 359–360 (1989).

Liedberg, Hans, Scandinavian Journal of Urology and Nephrology, Suppl. No. 124, pp. 1–43 (1989).

Mermel et al., The Journal of Infectious Diseases, vol. 167, pp. 920–924 (Apr. 1993).

Oloffs et al., Biomaterials, vol. 15, No. 10, pp. 753–758 (1994).

Riley et al., The American Journal of Medicine, vol. 98, pp. 349–356 (Apr. 1995).

Rungby, Jorgen, Danish Medical Bulletin, vol. 37, No. 5, pp. 442–449 (Oct. 1990).

Sioshansi, Piran, Artificial Organs, vol. 18, No. 4, pp. 266–271 (1994).

Tobin et al., Surfaces in Biomaterials, pp. 19–22 (1995).

Tweden et al., J. Heart Valve Dis., vol. 6, No. 5, pp. 553–561 (Sep. 1997).

M. Rabaud, J.Y. Elie, F. Lefebvre and D. Ducassou, A New Biodegradable Elastin–Fibrin Material; Its Use In Urological, Digestive And Cardiovascular Surgery, *Journal of Biomaterials Applications* vol. 7—Jul. 1992.

Ooyama et al, "Substratum–Bound Elastin Peptide Inhibits Aortic Smooth Muscle Cell Migration in Vitro", Arteriosclerosis 7(6):593–598 (1987).

Long et al, "Elastin Repeat Peptides as Chemoattractants for Bovine Aortic Endothelial Cells", Journal of Cellular Physiology 140:512–518 (1989).

Aprahamian et al, "A new reconstituted connective tissue matrix: Preparation, biochemical, structural and mechanic studies", Hournal of Biomedical Materials Research 21:965–977 (1987).

Rabaud et al, "Soluble Fibrinogen Derivatives Generated by Thrombin: Affinity for Elastin", Thrombosis Research 43:205–211 (1986).

Martin et al, "Biochemical study of adduct synthesis between fibrin monomers and elastin", Biomaterials 9:519–524 (1988).

Lefebvre et al, "New artificial connective matrix–like structure made of elastin solubilized peptides and collagens: elaboration, biochemical and structural properties", Biomaterials 13(1):28–33 (1992).

Pool et al, "Production of High–Potency Concentrations of Antihemophilic Globulin in a Closed–Bag System", The New England Journal of Medicine 273(27):1443–1447 (1965).

Landsman et al, "Light–absorbing properties, stability, and spectral stabilization of indocyanine green", Journal of Applied Physiology 40(4):575–583 (1976).

Crissman, Robert S., "Comparison of Two Digestive Techniques for Preparation of Vascular Elastic Networks for SEM Observation", Journal of Electron Microscopy Technique 6:335–348 (1987).

Guisti et al, "Bioartificial Polymeric Materials: A New Method to Design Biomaterials by using both Biological and Synthetic Polymers", TRIP 1(9):261–267 (1993).

MEDICAL ARTICLE WITH ADHERED ANTIMICROBIAL METAL

FIELD OF THE INVENTION

The invention relates to medical articles having elemental metal and/or metal compounds associated with biocompatible material, where the elemental metal or metal composition is effective as an antimicrobial agent. The invention also relates to processes for associating the elemental metal or metal compound with the medical article.

BACKGROUND OF THE INVENTION

A variety of medical articles are designed particularly for contact with a patient's bodily fluids. The duration of this contact may be relatively short, as is typical with wound dressings, or may be long term, as is typical with prosthetic heart valves implanted into the body of a recipient. Some articles such as catheters can have either short term or relatively long term contact. Other articles typically having relatively short term contact with the patient include, without limitation, burn dressings and contact lenses. Other articles typically having long term contact with a patient include, without limitation, prostheses.

Contact of exogenous articles with bodily fluids creates a risk of infection. This risk can be very serious and even life threatening. In addition, considerable costs, and longer or additional hospital stays may result due to infection. For example, infections associated with dressings can increase the seriousness of the injury for burn victims. Also, infection associated with an implanted prosthesis can necessitate replacement of the device.

Infections are a particularly common complication resulting from the use in hospitals of percutaneous devices such as catheters. Infections related to catheter use can result from intracutaneous invasion during catheter insertion or from invasion by way of the exit site during use. Adherence of bacteria to the catheter surface complicates treatment of the infection.

Prostheses, i.e., prosthetic articles, are used to repair or replace damaged or diseased organs, tissues and other structures in humans and animals. Prostheses generally must be biocompatible since they are typically implanted for extended periods of time. Examples of prostheses include, without limitation, prosthetic hearts, prosthetic heart valves, ligament repair materials, vessel repair and replacement materials, and surgical patches. A variety of prostheses incorporate tissue as at least a component of the prosthesis.

Physicians use a variety of prostheses to correct problems associated with the cardiovascular system, especially the heart. For example, the ability to replace or repair diseased heart valves with prosthetic devices has provided surgeons with a method of treating heart valve deficiencies due to disease and congenital defects. A typical procedure involves removal of the natural valve and surgical replacement with a mechanical or bioprosthetic valve. Another technique uses an annuloplasty ring to provide structural support to the natural annulus of the valve.

Prosthetic Valve Endocarditis (PVE) is an infection that can be associated with a heart valve prosthesis. Bacteria can form colonies at the surgical site associated with the implant and in the fabric of the sewing cuff of the valve prosthesis. The growth of tissue into the sewing cuff material also is associated with the attachment of bacteria and other pathogens. For this reason, heart valve recipients are cautioned regarding activities that may introduce bacteria into the bloodstream, such as dental work. For tissue replacement valves, PVE more commonly is associated with the leaflet portion of the valve rather than the sewing cuff portion of the valve.

PVE can be caused by gram-negative bacteria, gram-positive bacteria, fungi or rickettsia. PVE caused by gram-positive bacteria is particularly prevalent. Diagnosis is based generally on two positive blood cultures for the same organism along with compatible clinical symptoms. Certain organisms are difficult to culture, however, which can complicate diagnosis.

With respect to replacement heart valves, care must be taken to ensure sterility during production and to prevent contamination during the replacement valve implantation process. For example, to ensure sterility or to reduce perioperative contamination, some surgeons apply antibiotics to the prosthesis prior to implantation. These techniques, however, have relatively short-term effectiveness. In spite of these efforts, PVE occurs in about 2 percent to 4 percent of patients.

Infections occurring within the first 90 days after valve replacement are termed early onset PVE while infections occurring more than 90 days after valve implantation are termed late onset PVE. Mortality rates for early onset PVE range from 56 percent to 88 percent. Mortality rates for late onset PVE can be greater than 20 percent. These high mortality rates emphasize the seriousness of these infections. Similar infections are associated with other prostheses.

SUMMARY OF THE INVENTION

Improved procedures involve associating antimicrobial elemental metal and/or metal compounds with a medical article. The antimicrobial elemental metal or metal compound generally is associated with biocompatible material that can contact bodily fluids in use. In particular, antimicrobial elemental metal can be placed within a tissue specimen. Several approaches are described for depositing elemental metal and/or metal compounds in contact with the biocompatible material to inhibit infection at potential locations for microbial colonization. A combination of metals and/or metal compounds can be effectively used to provide short term inhibition of infection along with continuing antimicrobial activity for extended periods of time.

In a first aspect, the invention features a medical article including tissue, the tissue including a deposit of at least about 0.01 mg of antimicrobial elemental metal per gram of tissue. The medical article can be a heart valve prosthesis. The tissue can be crosslinked tissue or uncrosslinked tissue. The tissue preferably includes a deposit of at least about 0.5 mg of elemental silver per gram of tissue.

The tissue can further include a deposit of an antimicrobial metal compound, the metal compound having a solubility in water of less than about 0.01 moles per liter. In some embodiments, the metal compound is disposed within the tissue in regions effectively inaccessible to light. The tissue preferably includes a deposit of at least about 0.5 mg of metal compound per gram of tissue.

In another aspect, the invention features a method including distributing a medical article of the invention for use under the supervision of a health care professional.

In another aspect, the invention features a method of modifying tissue comprising the step of depositing antimicrobial elemental metal on and within the tissue. If the tissue is crosslinked with a multifunctional aldehyde, the depositing step can involve contacting crosslinked tissue with $Ag^+$ ions. In some embodiments, the deposition of antimicrobial elemental metal includes the steps of:

contacting the tissue in a solution of dissolved metal cations with a precipitation agent to form a metal compound precipitate, the metal compound precipitate being sensitive to reduction by light; and exposing the tissue, following the precipitation of the metal compound, to light to reduce the metal compound to elemental metal.

The metal cations can be silver cations, where the precipitation agent is selected from the group consisting of $Cl^-$, $Br^-$, $I^-$, alkyl halides, $PO_4^{-3}$, and $CO_3^{-2}$.

In other embodiments, the depositing step includes placing the tissue in a solution of metal ions; and applying a voltage to the tissue to deposit elemental metal in contact with the tissue. Preferably, at least about 0.05 mg of silver metal is deposited per gram of tissue.

In another aspect, the invention features a medical article including biocompatible material, the biocompatible material including a deposit of at least about 0.01 mg of elemental silver per gram of biocompatible material, and at least about 0.01 mg of corresponding metal compound per gram of biocompatible material at a location effectively isolated from exposure to light. The elemental metal can be elemental silver and the corresponding metal compound can be a silver halide.

In another aspect, the invention features a method of producing a medical article including a biocompatible material, the method comprising the step of adding a precipitation agent to the biocompatible material in contact with a solution of metal ions to deposit a first antimicrobial metal compound on and within the biocompatible material. The biocompatible material can include fabric and/or tissue. The metal compound can include a metal constituent that is selected from the group consisting of compounds of Ag, Au, Pt, Pd, Ir, Cu, Sn, Sb, Bi, Zn and combinations thereof. The metal compound preferably has a solubility in water of less than about 0.01 moles per liter.

The method can further include the step of adding a second precipitation agent to deposit a second antimicrobial metal compound on and within the biocompatible material. The second antimicrobial compound preferably has a solubility in water of at least about five time greater than the solubility in water of the first antimicrobial compound.

Other features and advantages of the invention will be apparent from the following detailed description of the invention and the claims.

DETAILED DESCRIPTION

New approaches are described to associate antimicrobial metal and/or metal compounds with medical articles that contact bodily fluids. In particular, tissue components of medical articles can be provided with adhered elemental metal and/or metal compounds. The association of antimicrobial elemental metal and/or metal compounds with the medical articles inhibits the development of infection. Suitable antimicrobial metals include, for example, Ag, Au, Pt, Pd, Ir, Cu, Sn, Sb, Bi, Zn and combinations thereof. The effectiveness of antimicrobial elemental metals is thought to be due to the slow formation of corresponding metal ions.

A variety of medical articles can be used to contact bodily fluids of a patient. Relevant medical articles generally incorporate a biocompatible material which is intended to contact the patient's biological fluids and/or tissues. Bodily fluids include, for example, blood, plasma, serum, interstitial fluids, saliva and urine. The patient can be an animal, especially a mammal, and preferably is a human.

Improved methods for associating antimicrobial elemental metals and/or metal compounds with medical articles generally involve directly depositing antimicrobial metals on and within tissue and/or other biocompatible materials. With respect to antimicrobial metal compounds, the compound can be deposited by adding a precipitation agent to the biocompatible material while the biocompatible material is incubating in a soluble metal solution. The antimicrobial metal compound that is precipitated generally must be relatively insoluble in water or other appropriate solvent. The precipitation agent causes a relatively insoluble metal compound to come out of solution into and onto the tissue or other biocompatible material.

In addition to, or as an alternative to metal compound deposition, elemental metal can be deposited. Using traditional methods, a substrate receiving a coating of elemental silver must withstand harsh, vacuum conditions generally used in the deposition of the silver metal. Tissue, in particular, generally cannot withstand these harsh conditions.

Three approaches are described for associating elemental metal with tissue and other biocompatible materials under relatively mild conditions. A first approach involves the reaction of metal solutions with a chemical reductant, such as unreacted crosslinking agent, which may be present in or added to the tissue the tissue. A second approach involves photoreduction of metal compounds in the presence of a biocompatible material. Finally, elemental metal can be deposited by electrochemical reduction.

The formation of antimicrobial elemental metal or of relatively insoluble deposits of metal compound on biocompatible material, such as tissue, can provide relatively long term protection from infection as well as directed protection for shorter periods. Long term protection is especially important for the function of prostheses and the like which remain in contact with a patient's bodily fluids for an extended period of time. Furthermore, the use of deposits of selected metal compounds can be used to design the article with a rate of antimicrobial metal release appropriate for the particular article. An appropriate release rate can be selected based on the length of time that the article generally contacts bodily fluids. A combination of deposited antimicrobial agents can yield improved prevention of infection relative to a single antimicrobial agent, especially to improve the overall effectiveness of the antimicrobial activity over time.

While reducing the risk from infection, the patient's plasma levels of the corresponding metal ions should stay safely below toxic levels. Healthy humans generally have, for example, plasma levels of Ag of about 0.2 $\mu$g/l to about 10 $\mu$g/l, where 10 $\mu$g/l corresponds to about 0.01 ppm or 10 ppb. In the blood, silver ions are carried by high molecular weight proteins, such as glutathione and transferrin. Silver cations are removed from the body with about 90 percent being excreted in bile and significant amounts being excreted in urine. Plasma levels of silver in sheep resulting from implantation of silver coated polyester have been evaluated. See, K. S. Tweden et al., J. of Heart Valve Disease, 6:553–561 (1997).

Serum silver ion concentrations of about 300 ppb have been associated with toxic symptoms including argyria in gingiva and cheeks, nephrotic syndrome and leukopenia. Silver ion concentrations of about 40 $\mu$mol/l (about 4 mg/l) are known to cause rapid cell death. Therefore, it is preferable to keep silver and other metal ion concentrations in the blood stream safely below toxic levels and preferably below levels where any symptoms are observable.

A. Biocompatible Article

Relevant biocompatible articles include all medical articles that contact bodily fluids. These articles can be organized roughly into three groups: implanted devices, percutaneous devices and cutaneous devices. Implanted devices broadly include articles that are fully implanted in a patient, i.e., are completely internal. Percutaneous devices include items that penetrate the skin, thereby extending from outside the body into the body. Cutaneous devices are used superficially, for example, at a wound site or at a moist membrane.

Implanted devices include, without limitation, prostheses such as transplant organs, heart valve prostheses, pericardial patches, vascular grafts, biological conduits, annuloplasty rings, bone, skin, ligaments and tendons. Percutaneous devices include without limitation catheters of various types. Catheters can be used for accessing various bodily systems such as the vascular system, the gastrointestinal tract, or the urinary system. Cutaneous devices include, without limitation, skin grafts, burn dressings, wound dressings of all types, and contact lenses. These biocompatible articles can be made from the biocompatible materials described below.

B. Biocompatible Material

Appropriate biocompatible materials include natural materials, synthetic materials and combinations thereof. Natural, i.e., biological, material for use in the invention includes relatively intact (cellular) tissue as well as decellularized tissue. These tissues may be obtained from, for example, natural heart valves; portions of natural heart valves such as roots, walls and leaflets; pericardial tissues such as pericardial patches; connective tissues; bypass grafts; tendons; ligaments; skin patches; blood vessels; cartilage; dura matter; skin; bone; umbilical tissues; and the like.

Natural tissues are derived from a particular animal species, typically mammalian, such as human, bovine, porcine, seal or kangaroo. These natural tissues generally include collagen-containing material. Natural tissue is typically, but not necessarily, soft tissue. Appropriate tissues also include tissue equivalents such as tissue-engineered material involving a cell-repopulated matrix, which can be formed from a polymer or from a decellularized natural tissue.

Biological tissues can be fixed by crosslinking. This provides mechanical stabilization, for example, by preventing enzymatic degradation of the tissue. Glutaraldehyde is typically used for fixation, but other fixatives can be used, such as epoxides, formaldehyde and other difunctional aldehydes. Biological materials can be used in either crosslinked or uncrosslinked form, depending on the type of tissue, the use and other factors.

Relevant synthetic materials include, for example, polymers and ceramics. Appropriate ceramics include, without limitation, hydroxyapatite, alumina and pyrolytic carbon. Polymeric materials can be fabricated from synthetic polymers as well as purified biological polymers. Appropriate synthetic materials include hydrogels and other synthetic materials that cannot withstand severe dehydration.

Appropriate synthetic polymers include without limitation polyamines (e.g., nylon), polyesters, polystyrenes, polyacrylates, vinyl polymers (e.g., polyethylene, polytetrafluoroethylene, polypropylene and poly vinyl chloride), polycarbonates, polyurethanes, poly dimethyl siloxanes, cellulose acetates, polymethyl methacrylates, ethylene vinyl acetates, polysulfones, nitrocelluloses and similar copolymers. These synthetic polymeric materials can be woven into a mesh to form a matrix or substrate. Alternatively, the synthetic polymer materials can be molded or cast into appropriate forms.

Biological polymers can be naturally occurring or produced in vitro by, for example, fermentation and the like. Purified biological polymers can be appropriately formed into a substrate by techniques such as weaving, knitting, casting, molding, extrusion, cellular alignment and magnetic alignment. For a description of magnetic alignments see, for example, R. T. Tranquillo et al., Biomaterials 17:349–357 (1996). Suitable biological polymers include, without limitation, collagen, elastin, silk, keratin, gelatin, polyamino acids, cat gut sutures, polysaccharides (e.g., cellulose and starch) and copolymers thereof.

Biocompatible materials can include a combination of the various natural materials and synthetic materials described above. The biocompatible materials also can include metal portions, and some relevant prostheses are made completely from metal, ceramics or a combination of metal, ceramics and, optionally, additional natural or synthetic materials. Mechanical heart valves are relevant products, which generally are made from metallic and/or ceramic components.

C. Deposited Metal Compounds

The deposition of metal compounds into a biocompatible material involves the formation of insoluble precipitants involving antimicrobial metal ions. Suitable antimicrobial metal ions include, for example, ions of Ag, Au, Pt, Pd, Ir, Cu, Sn, Sb, Bi, Zn and combinations thereof. The biocompatible material first is incubated in a solution of a soluble metal composition. A precipitation agent is added to the incubating biocompatible material such that an insoluble metal compound precipitates from solution forming a deposit of the insoluble compound generally on or in portions of the biocompatible material contacting the solution.

The soluble metal salt compositions may be unstable due to decomposition in light. It may be desirable to keep the soluble salt solutions in the dark as well as initially incubating the biocompatible material with the soluble salt solutions in the dark.

Preferred metal compositions include silver compositions. For example, the biocompatible material can be incubated with silver nitrate. Then, a chloride salt, such as sodium chloride, can be added to precipitate silver chloride. Similarly, a bromide salt, such as sodium bromide, can be used to precipitate silver bromide, which is about an order of magnitude less soluble than silver chloride. A variety of other salts can be used to precipitate silver including, for example, $I^{-1}$, $CO_3^{-2}$ and $PO_4^{-3}$. Organic precipitation agents can also be used. For example, organic halides that react by way of an $S_N1$ nucleophilic substitution can form precipitates of silver halide. Suitable organic halides generally include tertiary alkyl halides, allylic halides and benzylic halides.

Other compounds similarly can be precipitated based on other antimicrobial metals. For example, biocompatible material can be incubated with soluble cupric nitrate or cupric sulfate. Then, for example, stearic acid or diammonium hydrogen phosphate, $(NH_4)_2HPO_4$, can be added to the solution to precipitate cupric stearate or cupric phosphate, respectively. Similarly, the biocompatible material can be incubated with water soluble zinc compounds such as zinc chloride or zinc nitrate. Suitable precipitation agents include, for example, phosphates and stearic acid. Palladium diacetate can be precipitated from palladium chloride by the addition of acetic acid or a salt of acetic acid. Similar precipitations can be performed with other antimicrobial metal compounds based on relative insolubility of the compound.

For some metals, the precipitation agent can act by reducing the metal to a less soluble cation. For example, cupric ions ($Cu^{+2}$) are reduced by aldehydes to form cuprous ions ($Cu^{+1}$). A traditional reagent for this reaction is cupric tartrate ($CuC_4O_6H_4$), "Fehling's solution." Generally, insoluble CuO is formed. The aldehyde can be supplied by way of an unreacted crosslinking agent bound to the biocompatible material or as a separately added reagent.

The precipitated antimicrobial metal compound is selected based on the desired antimicrobial activity. This may involve a balance of several different factors. A significant factor is sufficient dissolution of the metal composition such that a desired amount of antimicrobial effectiveness is reached. At the same time, the precipitated compound should not dissolve too rapidly so that the antimicrobial effectiveness is too short lived or that toxic levels of metal are reached. A mixture of relatively insoluble salts can be used effectively to form a desired antimicrobial activity, as described further below.

The rate of dissolution of a metal compound is influenced by the solubility of the metal compound as well as kinetic factors. The rate of dissolution generally depends on the conditions in which the biocompatible material is placed. Typically, the biocompatible material is not kept at equilibrium conditions since fluid generally flows over the biocompatible material such that antimicrobial metal ions are removed. Therefore, the rate at which the metal ions are removed depends on the particular use.

Generally, suitable metal compounds have a solubility in water of less than about 0.01 moles/liter, preferably less than about 0.001 moles/liter, and for more long term applications less than about 0.0001 moles/liter. For use in prostheses that can benefit from antimicrobial activity over several years, even less soluble metal compositions can be used effectively. Similarly, less soluble metal compositions would be suitable for use with biocompatible materials that are subject to continuous fluid flow. Information regarding the kinetics of dissolution in water generally is known but is not systematically quantified. Empirical evaluations can be performed to determine the rate that the metal ions are removed in particular applications.

The quantity of precipitated metal compound generally is selected to yield, to the extent possible, a suitable amount of antimicrobial activity for a desired length of time. The amount of deposited metal compound should not interfere significantly with important mechanical properties of the biocompatible material. If the conditions for depositing the metal salt are relatively harsh, it may be desirable to limit the exposure time while accepting a corresponding decrease in deposited metal compound. The amount of antimicrobial metal compound generally is greater than about 0.01 mg per gram of dry biocompatible material, and preferably from about 0.05 mg to about 40 mg per gram of dry biocompatible material, and more preferably from about 0.1 mg to about 20 mg/gram of dry biocompatible material.

D. Deposited Metal

Elemental metal can be deposited as an alternative to or in addition to depositing metal compounds. As in the case of forming deposits of metal compounds, the biocompatible material is initially contacted with a solution of metal salt. Chemical, photochemical or electrochemical approaches can then be implemented to reduce the metal to form deposits of elemental metal in contact with the biocompatible material.

Chemical reduction approaches involve a reaction of a metal compound with a chemical compound that reduces the metal ions to elemental metal. This approach is similar to the approach described above using a reducing agent to transform one metal cation to another metal cation that is less soluble with respect to the anions present in the solution. For example, aldehydes are known to reduce silver ions to elemental silver. The traditional reagent for this reaction is ammoniacal silver hydroxide ($Ag(NH_3)_2OH$), "Tollens' reagent." Aldehydes can be supplied as partially unreacted multifunctional aldehyde compounds, such as crosslinking agents, or as added aldehydes. Similarly, a palladium chloride solution can be reduced to form palladium metal using hydrogen or carbon monoxide (CO), which can be bubbled into the solution. Elemental copper can be precipitated from copper solutions by the addition of aluminum, iron or zinc particles. Similarly, reductants can be used to deposit other antimicrobial metals.

In the photochemical approach, light is used to reduce a metal compound to produce elemental metal in contact with the biocompatible material. For example, certain silver compounds are subject to reduction upon exposure to standard lighting conditions. In this approach, a metal first can be deposited in contact with the biocompatible material as a relatively insoluble metal compound that is then subjected to light, or the photochemical reaction can involve the light induced reduction of metal ions in solution without forming an insoluble metal compound. In either case, only the outer portion of the tissue generally is deposited with elemental metal since the biocompatible material can have portions in contact with the solution that are not easily exposed to light.

Electrochemical deposition involves the application of a voltage to the tissue in order to electroplate, from the metal solution, elemental metal in contact with the tissue. For example, to deposit silver metal from a silver solution requires the application of an applied voltage where the biocompatible material functions as a cathode. The required voltage depends on the counter reaction and the concentrations of ions in the solutions. The selection of the salt influences the effectiveness of the plating process. Silver plating works effectively with $[Ag(CN)_2]^{-1}$ present in solution.

While antimicrobial elemental metals generally are resistant to corrosion, the metals slowly ionize to function as antimicrobial agents. To determine a desired amount of metal to deposit, the rate of ionization is a significant factor to be considered. The environment in which the biocompatible material is placed is a significant factor in determining the rate of ionization. Given a particular rate of ionization, the amount of metal deposited establishes the length of time over which metal is available for ionization, with corresponding antimicrobial effectiveness.

With any method of deposition, the amount of deposited metal should not interfere significantly with important mechanical properties of the biocompatible material. If the conditions for depositing the elemental metal are relatively harsh, it may be desirable to limit the exposure time while accepting a corresponding decrease in deposited metal. The amount of antimicrobial metal generally is greater than about 0.01 mg per gram of dry biocompatible material, and preferably from about 0.05 mg to about 40 mg per gram of dry biocompatible material, and more preferably from about 0.1 mg to about 20 mg per gram of dry biocompatible material.

E. Processing Considerations

In general, the biocompatible material can be subjected to elemental metal or metal compound deposition prior to or following processing into a biocompatible article. For example, a tissue heart valve prosthesis can be treated to deposit antimicrobial metal either before or after attachment of a sewing cuff. Suitable solvents for antimicrobial metal deposition are generally aqueous although other solvents, such as alcohol, can be used if the biocompatible material is not damaged by the solvent.

As indicated above, the amount of metal or metal compound deposited on the biocompatible material can be influenced by the harshness of the conditions used to deposit the elemental metal or metal compound. For example, exposure to solutions with pH values significantly deviating from physiological values should be minimized. To the extent that the pH can be adjusted, it is preferred to keep the pH between values of about 6 and about 8.5, more preferably between about 7.0 and about 8.0. Ionic strength can be adjusted, if desired, by the addition of inert salts, the identity of which generally depends on the nature of the deposition process being used.

In any case, the mechanical properties of the biocompatible material, especially tissue, should not be significantly degraded by the antimicrobial metal deposition. In particular, the mechanical strength should not decrease significantly, and the material preferably maintains its flexibility.

There are certain situations where multiple biological activities are desirable. In these situations, materials can be made by forming a bioactive coating on a base material, where the bioactive coating can include, for example, cell adhesion molecules, anticoagulants such as heparin and hirudin, or growth factors such as the fibroblast growth factors, platelet-derived growth factors, transforming growth factors, epidermal growth factors, insulin-like growth factors I and II, platelet-derived endothelial cell growth factors, vascular endothelial growth factor, and combinations thereof.

Articles with bioactive coatings then can be subjected to further application of antimicrobial elemental metal or metal compounds using the techniques described herein. In some cases, the order of the application of the antimicrobial metal and the other bioactive material can be reversed, or the application of the antimicrobial metal and other bioactive material can be performed simultaneously. Performance may be influenced by the order of application of the different active agents, and in such cases, the order of application can be selected based on performance considerations.

F. Combination of Approaches

With implanted heart valve prostheses, the three month period immediately following implantation is a particularly significant period with respect to the prevention of infection since the greatest number of cases of PVE occur in this time period. Nevertheless, the risk of infection due to prosthesis implantation continues for a year or more. It may be possible to improve the overall effectiveness of antimicrobial treatments by combining two or more antimicrobial agents. For example, it may be desirable to combine one deposited compound having relatively high metal ion loss rate over the first two to three month period with another antimicrobial agent that provides continued antimicrobial effectiveness for a year or more. A third compound can be deposited that provides an especially large amount of antimicrobial ions during the first days or weeks from the implantation. Additional or alternative combinations of antimicrobial agents can be used, as desired.

There are a variety of ways of combining the methods herein. Two or more different metal compounds with different solubility constants can be precipitated onto the biocompatible material to provide two sources of antimicrobial metal ions with different dissolving rates. For example, silver bromide has a solubility less than a tenth the solubility of silver chloride. Therefore, a combination of silver chloride and silver bromide can result in an extended time of antimicrobial effectiveness relative to silver chloride alone and greater short term effectiveness than silver bromide alone. In a preferred embodiment, a second antimicrobial metal compound would have a solubility in water of at least five times greater than the solubility in water of a first antimicrobial metal compound. Generally, the compounds can be deposited sequentially or simultaneously by the concurrent addition of two or more precipitation agents.

Similarly, two or more different metals can be deposited, such as silver and copper. Generally, the deposition of two or more metals is done sequentially to minimize the cross reactivity during the reduction step. When two or more metals are deposited in contact with each other, the less easily oxidized metal is generally preserved by the preferential oxidation of the other metal until the more easily oxidized metal is consumed or no longer in electrical contact with the more stable metal.

Alternatively, a metal and a metal compound can both be deposited. This alternative is exemplified below where both silver metal and silver chloride are deposited. The silver metal results from the light induced reduction of the silver chloride to silver metal at the portion of tissue that is susceptible to light. The elemental metal and metal compound can be selected to provide effectiveness over different time periods. Additional metal and/or metal compounds can be included to incorporate more than two different antimicrobial agents.

With any of the methods involving multiple antimicrobial agents, the agents should be deposited such that the device, for example a heart valve prosthesis with components that must flex, maintains adequate mechanical properties. In addition, different parts of the biocompatible material can be associated with distinct antimicrobial agents, either metal compounds or elemental metal, to ensure adequate mechanical properties of the prosthesis. Similarly, whether one or more antimicrobial agents are deposited, only a portion or certain parts of the biocompatible material may be associated with the one or more antimicrobial agents such that other portions or parts are free of the antimicrobial agents.

Furthermore, the procedures described herein can be combined with other approaches to reduce microbial infection. For example, glutaraldehyde treatment is effective in reducing microbial contamination of medical articles. Glutaraldehyde can be used effectively even if it is not needed as a crosslinking agent. Similarly, immersing a medical article in alcohol or an aqueous alcohol solution can reduce microbial contamination.

Generally, the procedures described herein involve contacting the biocompatible material with a metal salt solution. Some metal ions generally associate themselves with functional groups within the biocompatible material. This additional form of treatment is a natural part of the procedures described herein.

Also, commonly assigned U.S. patent application Ser. No. 08/787,139, incorporated herein by reference, discloses a method of associating antimicrobial metal cations with exogenous storage structures, for example, metal storage proteins such as ferritin. The exogenous storage structures containing antimicrobial ions are then bound to biocompatible material. The procedures based on exogenous storage structures can be combined with the procedures described herein for depositing elemental metal and/or insoluble metal compounds in association with biocompatible material. The association of the exogenous storage structures with the biocompatible material can be performed before or after deposition of metal and/or metal compounds into the biocompatible material.

G. Combination with Anticalcification Agents

Polyvalent metal cations such as $Fe^{+3}$ and $Al^{+3}$ have been shown to be useful in reducing calcification that is associated with implanted prostheses. Exogenous storage structures have been shown to be useful in delivering these polyvalent cations. See, commonly assigned and copending U.S. patent application Ser. No. 08/690,661, incorporated herein by reference.

Alternatively, compositions including these polyvalent metal cations can be deposited into the biocompatible material along with the antimicrobial metal or metal composition. For example, aluminum palmitate can be precipitated from a solution of aluminum chloride by the addition of palmitic acid.

H. Storage, Packaging and Distribution

Following deposition of desired antimicrobial agents, the biocompatible material, possibly formed into a medical article, is stored. Preferred storage techniques minimize the risk of microbial contamination. For example, the biocompatible material can be stored in a sealed container with an aqueous glutaraldehyde solution. In a sealed container, the biocompatible material is not subjected to a continuous supply of fluids. As a result, the solution generally comes to equilibrium with the deposited antimicrobial agent.

Still, due consideration should be given to possible loss over time of the deposited antimicrobial agent during storage. If excessive amounts of antimicrobial agent would be absorbed into the storage solution, the storage time should be selected such that the amount of antimicrobial agent lost from the biocompatible material is within a satisfactory level. Additives can be added to the storage solution to reduce the loss of antimicrobial agents, such as silver nitrate if silver compounds are deposited in the biocompatible material or antioxidants such as ascorbic acid if elemental metals are deposited.

For distribution, the medical articles are placed in sealed and sterile containers. The containers are generally dated such that the date reflects the maximum advisable storage time accounting for possible degradation of the antimicrobial agents as well as other factors. The containers are distributed to health care professionals for use in appropriate medical procedures such as implantation of a prosthesis and the like.

EXAMPLES

In the following examples, the silver nitrate was ACS reagent grade 99+% pure, distributed by Aldrich Chemical Co., Milwaukee, Wis. Purified water used was purified by reverse osmosis and had a resistivity of 10 megaohms per cm or greater. The photographs in FIGS. 1–8 are at a magnification from about 4x to about 6x, except for FIG. 3 which has a magnification of about 40x.

Example 1

Aldehyde Reduction

Tissue samples were glutaraldehyde-crosslinked, porcine aortic tissue. To prepare a solution for each tissue sample, a 10.0 ml quantity of 5 percent weight/volume silver nitrate and a 5.0 ml quantity of 10 percent sodium hydroxide was placed into a glass test tube. A gray precipitate of silver oxide resulted. Then, a 2.5 ml quantity of 2.8 percent aqueous ammonium hydroxide (ammonia) solution was added to the test tube. The tube was stoppered and shaken. Additional quantities totaling 3.0 ml of ammonium hydroxide solution were added to the tube, and the tube was shaken until almost all of precipitate was dissolved. In total, 5.5 ml of ammonium hydroxide were added to each tube. The resulting solution in the tube had a pH of 11.6.

The 5 percent weight per volume silver nitrate solution was prepared by mixing 5 grams of silver nitrate with sufficient pure water to fill a 100 ml volumetric flask. Following standard notation in the field, the sodium hydroxide solution was prepared by 1 to 5 volume dilution with purified water of a 50 percent by weight NaOH solution from CSM Chempure, Houston, Tex. Similarly, the 2.8 percent ammonia solution was prepared by 1 to 10 volume dilution with purified water of a 28 percent by weight ammonia solution from Mallinckrodt, Paris, Ky.

Glutaraldehyde treated aortic valve leaflets and 8 mm aortic wall biopsy punches were each placed in separate test tubes that were prepared with ammoniacal silver hydroxide as described in the last paragraph. Equivalent tissue samples were not placed in the test tubes for use as controls. The cardiac tissues were received from an FDA approved abattoir. To prepare the tissues, the tissues were cleaned of fat and rinsed in 0.9 percent saline (Baxter, Deerfield, Ill.) overnight to remove blood and other debris. The tissue samples were placed in a 0.5 percent HEPES buffered, glutaraldehyde solution. The samples were incubated in this solution for approximately one month. The 0.5 percent HEPES buffered, glutaraldehyde solution was prepared by placing 3.86 9 NaCl (Fisher Scientific, Springfield, N.J.), 11.92 g HEPES buffer (Sigma Chemical Co., St. Louis, Mo.), and 10 ml 50 percent by weight glutaraldehyde solution (EM Science, Ft. Washington, Pa.) in a 1.0 liter volumetric flask along with sufficient pure water to file the flask to the one liter mark.

A 10 ml quantity of 5 percent by weight formaldehyde solution was added to the tube to plate out the silver. The 5 percent formaldehyde solution was prepared by mixing 1.35 ml of 37 percent formaldehyde solution (Sigma Chemical Co., St. Louis, Mo.) with sufficient pure water to fill a 10 ml volumetric flask. The tissue was incubated for a total of 30 seconds. The relatively short incubation time was selected to minimize any detrimental effect on the tissue from the alkaline pH. Following removal from the ammoniacal silver hydroxide solutions, the tissue samples were rinsed and soaked sequentially in three 50 ml quantities of purified water for 5 min., 2 hours and 24 hours, respectively. The silver deposited tissue samples did not appear mechanically degraded or less flexible than untreated control samples.

Figure 1:
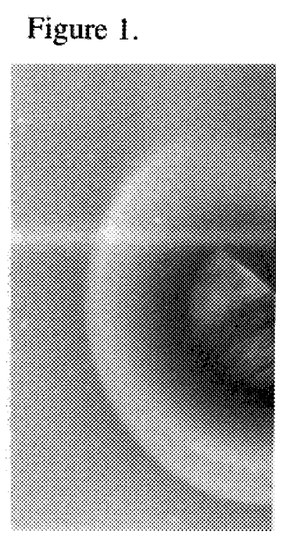
FIG. 1 is a top view of tissue with deposited elemental silver on a plate with an active culture of S. epidermidis.
Figure 2:
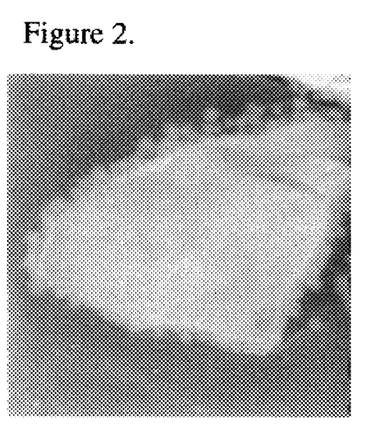
FIG. 2 is a top view of control tissue on a plate with an active culture of S. epidermidis.

A portion of the samples were sent for histological examination. Following rinsing, the remaining silver deposited tissue samples were placed on plates with active cultures of *Staphylococcus epidermidis*, *Bacillus subtilis*, or *Escherichia coli* bacteria. *Staphylococcus epidermidis* is the most common etiological agent for early PVE. Generally, one tissue sample was placed on each plate. The tissue samples demonstrated very good antimicrobial properties after 24 hours of incubation as demonstrated by a region free from bacterial growth ringing the tissue samples, as shown in FIG. 1. Control samples of the same glutaraldehyde treated tissue without the silver treatment were infected with the bacterial cultures, as shown in FIG. 2.

Example 2

Salt Precipitation and Reduction

A 10.0 ml quantity of 5 percent aqueous silver nitrate solution, as described in Example 1, was placed in a glass test tube. Tissue samples included glutaraldehyde-crosslinked, porcine aortic leaflets, porcine aortic wall and bovine pericardium. The tissue samples were prepared as described in Example 1. The tissue samples were separately incubated in tubes containing the silver nitrate. Silver nitrate is thought to be relatively benign with respect to tissue, and dilute silver nitrate has been used for topical applications, for example, for eyes, mouth ulcers, and irrigation of the bladder and urethra.

Following the 30 minute incubation, the samples were removed from the silver nitrate and placed in 50 ml of a 0.9 percent by weight aqueous saline (NaCl) solution (Baxter, Chicago, Ill.) to precipitate out the silver as AgCl. The saline was replaced after five minutes and again after another 15 minutes. Half of the samples were kept in the saline and exposed to light for about one week to reduce the exposed silver compounds to silver metal. Silver deposits were visible on the tissue within five hours of incubation. The other half of the silver treated samples were removed from the saline and placed in 10 percent formalin (formaldehyde and ethanol) from Fisher Chemical, Fairlawn, N.J. The samples in formalin similarly were exposed to light to reduce silver salt to silver metal.

Figure 3:
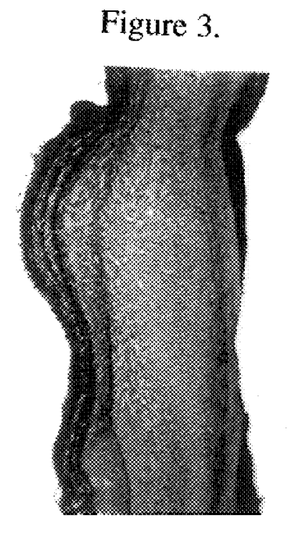
FIG. 3 is a cross section of heart valve leaflet tissue with deposited AgCl and with H & E stain, the surface portion of the tissue having been reduced with light to elemental silver.
Figure 4:
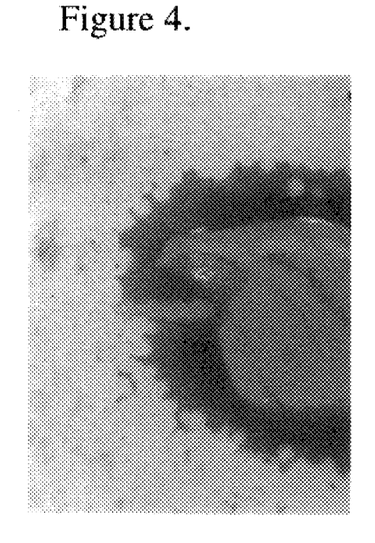
FIG. 4 is a top view of tissue on a plate with an active culture of B. subtilis, the tissue having deposited AgCl and elemental silver produced by reduction with light while in a salt solution.
Figure 5:
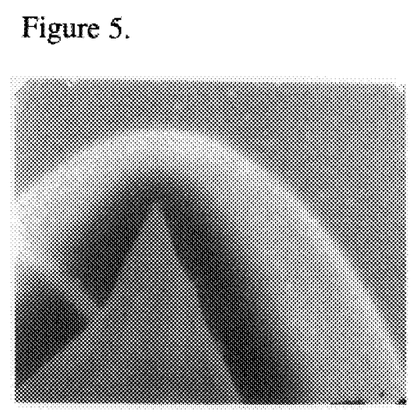
FIG. 5 is a top view of tissue on a plate with an active culture of S. epidermidis, the tissue having deposited AgCl and elemental silver produced by reduction with light while in a saline solution.
Figure 6:
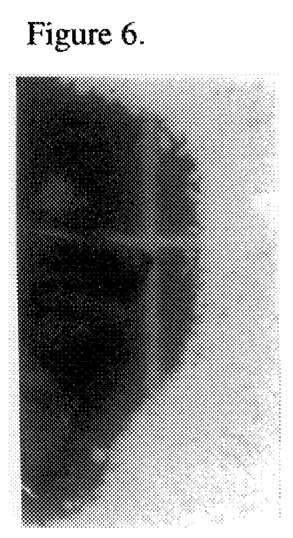
FIG. 6 is a top view of tissue on a plate with an active culture of B. subtilis, the tissue having deposited AgCl and elemental silver produced by reduction by light while in a formalin solution.
Figure 7:
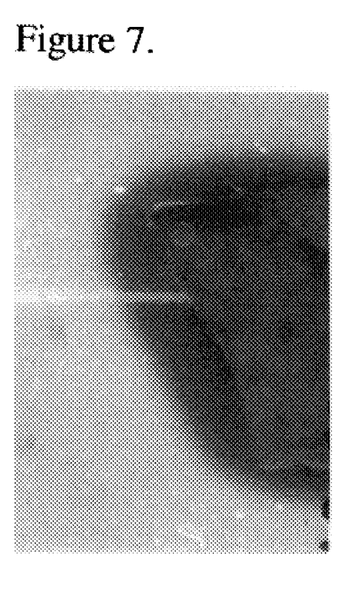
FIG. 7 is a top view of tissue on a plate with an active culture of S. epidermidis, the tissue having deposited AgCl and elemental silver produced by reduction by light while in a formalin solution.

The tissue samples reduced in the saline solution were brownish in color while the tissue samples reduced in the formalin were gray in color. The tissue samples did not appear mechanically degraded or less flexible than control samples. Referring to FIG. 3, cross sections of the leaflets reveal that elemental silver was localized in a band of tissue near the surface. The inner portions of the tissue had deposits of silver chloride. Presumably, sufficient light does not penetrate to the inner portions of the tissue to reduce significant quantities of the silver chloride to elemental silver.

Figure 8:
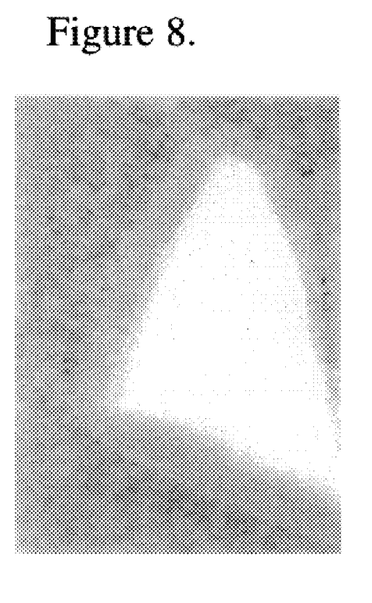
FIG. 8 is a top view of control tissue on a plate with an active culture of B. subtilis.

Leaflet samples from both the saline containing tubes and the formalin containing tubes were placed on plates with active cultures of *Bacillus subtilis* bacteria and *Staphylococcus epidermidis* bacteria. Referring to FIGS. 4–7, the tissue samples demonstrated very good antimicrobial properties as demonstrated by a region free from bacterial cultures ringing the tissue samples. Control samples of the same glutaraldehyde treated tissue without the silver treatment were infected with the bacterial cultures, as shown in FIGS. 2 and 8.

Example 3

Implantation Studies

Nine samples were implanted into rats to evaluate the rate of silver loss from the tissue. Two samples were porcine aortic leaflets prepared according to Example 1 above. Two samples were 8 mm root punches from a porcine aortic wall prepared according to Example 1 above. Five samples were 8 mm punches from bovine pericardium prepared according to Example 2 above, with reduction performed in formalin. Samples from the same tissue specimens were retained for pre-implant evaluation. The nine samples were placed subcutaneously in the back of juvenile male rats using color coded suture. The samples were removed 21 days after implantation. Following removal, the samples were placed in 0.9% saline prior to analysis. Each tissue sample was removed from the saline and sectioned in half. One half portion of each tissue sample was cleaned of host tissue and used for elemental analysis. The second half portion of each tissue was placed in 10% formalin and stored for histological examination.

The amounts of silver in the tissue samples before and after implantation are presented in Table 1. Silver quantities were measured using an ICP-AES (Inductively Coupled Plasma-Atomic Emission Spectroscopy) instrument, an Atom Scan 16™ by Thermo Jarrell Ash Corp., Franklin, Mass.

TABLE 1

| Type of Tissue | Pre-implant (Ag mg/g of dry tissue) | Post implant (Ag mg/g of dry tissue) |
| --- | --- | --- |
| Ex. 1 Porcine Aortic Leaflet | 2.26 ± 0.53 | 2.00 ± 0.47* |
| Ex. 1 Porcine Aortic Wall | 2.42 ± 0.67 | 2.08 ± 0.86* |
| Ex. 2 Bovine Pericardium | 5.63 ± 0.72 | 5.25 ± 0.83 |

It can be seen that the quantity of silver deposited according to the procedure of Example 2 was about twice the quantity of silver deposited by the procedure of Example 1.

The embodiments described above are intended to be exemplary and not limiting. Other embodiments may be within the scope of the claims.

What is claimed is:

1. A medical article comprising tissue, said tissue comprising a deposit of at least about 0.01 mg of antimicrobial elemental metal per gram of tissue.

2. The medical article of claim 1, wherein said medical article comprises a heart valve prosthesis.

3. The medical article of claim 1, wherein said tissue comprises crosslinked tissue.

4. The medical article of claim 1, wherein said tissue comprises uncrosslinked tissue.

5. The medical article of claim 1, wherein said tissue comprises a deposit of at least about 0.5 mg of elemental silver per gram of tissue.

6. The medical article of claim 1, wherein said tissue further comprises a deposit of an antimicrobial metal compound, said metal compound having a solubility in water of less than about 0.01 moles per liter.

7. The medical article of claim 6, wherein said metal compound is disposed within said tissue in regions effectively inaccessible to light.

8. A method comprising distributing a medical article of claim 1 for use under the supervision of a health care professional.

9. A medical article comprising biocompatible material, said biocompatible material comprising a deposit of at least about 0.01 mg of elemental metal per gram of biocompatible material, and at least about 0.01 mg of corresponding metal compound per gram of biocompatible material at a location in the biocompatible material that is isolated from exposure to light not due to blockage of light by the deposit.

10. The medical article of claim 9, wherein said elemental metal is elemental silver and said corresponding metal compound is a silver halide.

11. The medical article of claim 1 wherein said antimicrobial elemental metal is selected from the group consisting of Ag, Au, Pt, Pd, Ir, Cu, Sn, Sb, Bi, and Zn.

12. The medical article of claim 1 wherein said antimicrobial elemental metal comprises silver (Ag).

13. The medical article of claim 1 wherein said tissue comprises a deposit of from about 0.05 mg to about 40 mg of elemental metal per gram of tissue.

14. The medical article of claim 1 wherein said tissue further comprises a deposit of a second elemental metal.

15. The medical article of claim 9 wherein said metal compound comprises an anion selected from the group consisting of $Cl^{-1}$, $Br^{-1}$, $I^{-1}$, $PO_4^{-3}$, and $CO_3^{-2}$.

16. The medical article of claim 9 wherein said biocompatible material further comprises a second metal compound.

17. The medical article of claim 9 wherein said metal compound has a solubility less than about 0.001 moles per liter.

18. The medical article of claim 9 wherein said biocompatible material comprises from about 0.1 mg to about 20 mg of metal compound per gram of biocompatible material.

19. The medical article of claim 9 wherein said antimicrobial elemental metal is selected from the group consisting of Ag, Au, Pt, Pd, Ir, Cu, Sn, Sb, Bi, and Zn.

20. The medical article of claim 9 wherein said biocompatible material comprises tissue.

* * * * *